(12) United States Patent
Vera et al.

(10) Patent No.: US 6,440,364 B1
(45) Date of Patent: Aug. 27, 2002

(54) METHOD OF DEGASSING ABSORBABLE SUTURE PRODUCTS

(75) Inventors: Luis E. Vera, Bergenfield, NJ (US); Robert J. Cerwin, Pipersville, PA (US); LeRoy Hugo Anderson, San Angelo, TX (US); Vincent Foerst, No. Plainfield, NJ (US); John J. Karl, Hopatcong, NJ (US); Lesley F. Traver, Branchburg, NJ (US); James Richard McDivitt, Flemington, NJ (US); Jimmy Dalton Webber, Cornelia, GA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/251,244

(22) Filed: Feb. 16, 1999

(51) Int. Cl.[7] .............................. A61L 9/00; A01N 2/07
(52) U.S. Cl. ............................ 422/33; 422/4; 422/28; 422/34; 422/36
(58) Field of Search ................................ 422/4, 26, 28, 422/33, 37, 34, 36

(56) References Cited

U.S. PATENT DOCUMENTS

| | | | | |
|---|---|---|---|---|
| 3,728,839 A | * | 4/1973 | Glick | .......................... 53/21 FC |
| 3,815,315 A | * | 6/1974 | Glick | .......................... 53/21 FC |
| 3,876,068 A | | 4/1975 | Sonnino | |
| 4,482,053 A | * | 11/1984 | Alpern et al. | ................ 206/439 |
| 4,990,131 A | * | 2/1991 | Dardik et al. | .................. 600/36 |
| 5,218,087 A | * | 6/1993 | Suzuki et al. | ................ 528/503 |
| 5,287,634 A | | 2/1994 | Hain et al. | |
| 5,464,580 A | * | 11/1995 | Popescu et al. | ................ 422/34 |
| 5,760,118 A | * | 6/1998 | Sinclair et al. | .............. 524/306 |
| 6,096,809 A | * | 8/2000 | Lorcks et al. | .................. 524/47 |

* cited by examiner

Primary Examiner—Robert J. Warden, Sr.
Assistant Examiner—Monzer R. Chorbaji
(74) Attorney, Agent, or Firm—Emil Richard Skula

(57) ABSTRACT

A method of sterilizing absorbable sutures using a sterilant gas such as ethylene oxide gas. The method utilizes a first degassing step, and a second degassing step at elevated temperatures to remove residual sterilant gas, diluent gas, by-products and moisture.

29 Claims, 2 Drawing Sheets

* Skip for Single Chamber Operation

* Skip for Single Chamber Operation

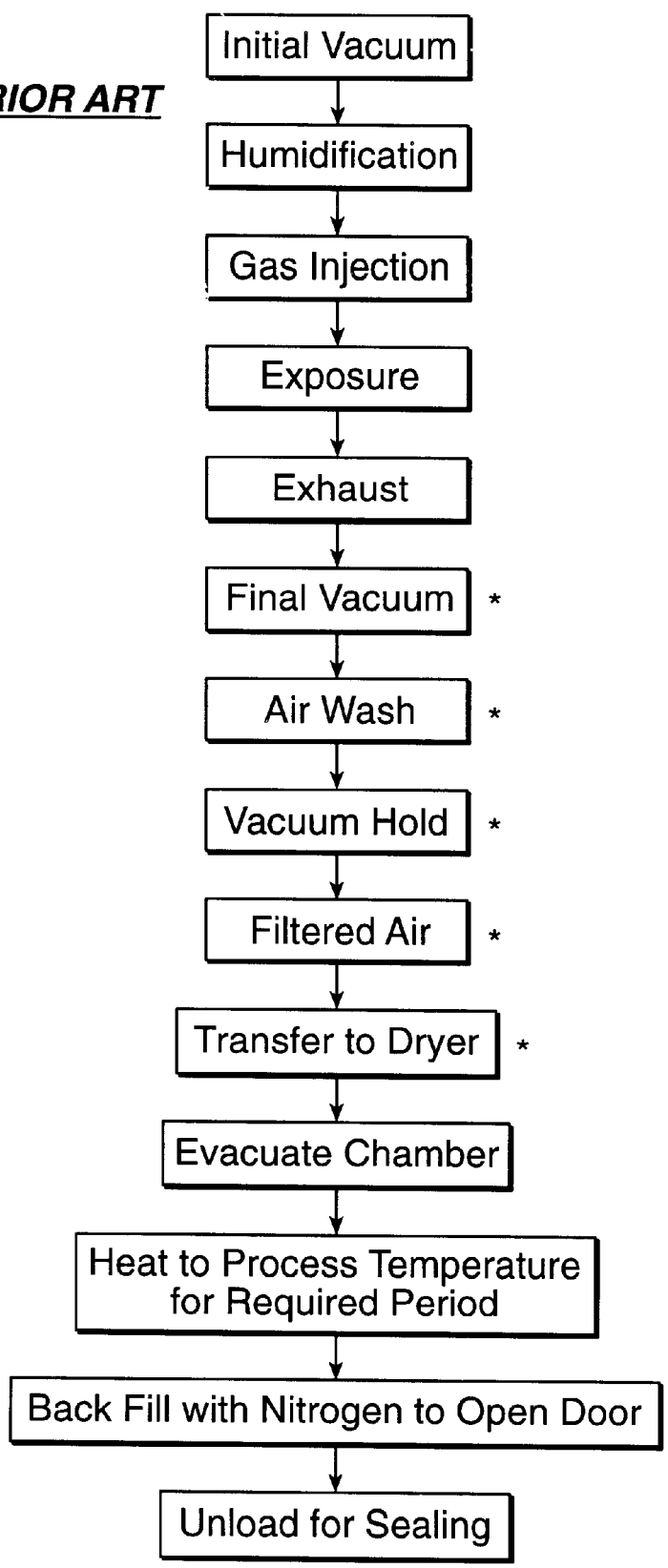
FIG. 2 _PRIOR ART_
* Skip for Single Chamber Operation

METHOD OF DEGASSING ABSORBABLE SUTURE PRODUCTS

TECHNICAL FIELD

The field of art to which this invention pertains is sterilization processes, in particular, ethylene oxide sterilization processes for medical devices manufactured from bioabsorbable polymers.

BACKGROUND OF THE INVENTION

Ethylene oxide sterilization processes useful to sterilize medical devices manufactured from bioabsorbable polymers, such as absorbable surgical sutures, have long been known in this art. Examples of such processes are contained in U.S. Pat. Nos. 3,728,839, 3,815,315, 3,876,068, 5,287,634 and 5,464,580. The medical devices can be made from conventional, known bioabsorbable materials such as aliphatic polyesters, polylactides, polygycolides and polylactones and the like. In a typical ethylene oxide sterilization process for surgical sutures, packaged surgical sutures are typically placed in a specially configured sterilization chamber. A vacuum is then placed upon the chamber to remove residual air from the packages containing the sutures. Then, humidity in the form of steam or water vapor is transported into the sterilizer chamber in a sufficient quantity such that the water vapor permeates the suture packages and contacts the interior of the packages as well as the sutures. Next, ethylene oxide gas sterilant is charged into the sterilizer chamber and diffuses into the interiors of the packages and contacts the package interiors and the sutures. The ethylene oxide gas acts as a sterilant or sterilizing agent. It is known that ethylene oxide gas is highly flammable and explosive. Accordingly, sterilization processes have been developed wherein the ethylene oxide gas is mixed with non-reactive gases which acts as a diluent. Such gases include nitrogen, Freon® gas, and new environmentally friendly products, which replace the older chlorofluorohydrocarbons such as GENETRON™ brand gas, which is a chlorofluorocarbon that is less likely to adversely affect the environment. The replacement of chlorofluorocarbons such as Freon® is desirable since it is believed that these compounds and entities may deplete ozone in the upper layers of the atmosphere.

Although the new diluent gases such as GENETRON™ serve adequately as a component of an ethylene oxide sterilant gas, it is known that there are some problems associated with their use. In particular, it is believed that GENETRON™ gas hydrogen bonds with plastics in packaging. This can be a problem particularly when degassing the sterilized medical device packages. The last stage of an ethylene oxide sterilization cycle is the degassing phase where it is necessary to degas or remove substantially all traces of the sterilant gas, diluent gas, sterilization by-products and moisture. Sterilization by-products in an ethylene oxide sterilization process are well known and include ethylene cholorhydrin, ethylene glycol, etc. This is accomplished by conventionally heating the interior of the sterilization chamber while pulling a vacuum on the sterilization chamber, or by placing the sterilized, packaged device into a separate degassing chamber and heating the interior of the chamber while pulling a vacuum. Heating the sutures in the chamber must be controlled to prevent possible degradation of the sutures. This may result in increased degassing times. Residual diluent gas in packaging materials may adversely affect seal integrity. Such a process is illustrated in FIG. 2.

What is needed in this art are new sterilization processes which can be used for the gas sterilization of bioabsorbable medical devices, such as absorbable sutures, which provide for the effective removal of sterilant gases, diluent gases, sterilization byproducts, and moisture without adversely affecting the packaging material or degrading the medical devices.

SUMMARY OF THE INVENTION

Accordingly, it is an object the present invention to provide a novel gas sterilization process useful with bioabsorbable medical devices, such as surgical sutures.

It is a further object of the present invention to provide such a process having improved efficiency while reducing the time needed to remove the residual sterilant gas, diluent gas, sterilization by-products and moistures during degassing cycles.

Therefore, a novel sterilization cycle is disclosed for gas sterilization of medical devices made from bioabsorbable medical devices. The process consists of initially providing a bioabsorbable medical device, such as a surgical suture, in a packaging pouch. Then, the medical device and pouch are placed in a chamber of a gas sterilant sterilizer. Next, a vacuum is pulled on the chamber and moisture is injected into the chamber. Then, a mixture of sterilant gas and an inert diluent is charged into the chamber and maintained for a sufficient time to effectively sterilize the device and the interior of the package. Then, the device and package are initially degassed by pulling a vacuum on the chamber, while increasing the temperature of the interior of the chamber to a first temperature and maintaining this temperature for a sufficient time to effectively remove substantially all of the moisture from the device and package. Finally, the device and package is degassed for a second time by pulling a vacuum on the chamber while increasing the temperature of the interior of the chamber to a second temperature , and maintaining that temperature for a sufficient time to effectively remove substantially all of the residual sterilant gas, diluent gas, sterilization by-products, and moisture from the device and package without degrading the bioabsorbable medical device.

These and other advantages and aspects of the present invention will become more apparent from the following description and accompanying drawings.

BRIEF DESCRIPTION OF THE DRAWINGS

FIG. 2 is a flow diagram of a sterilization process of the prior art using ethylene oxide as a sterilant gas.

DESCRIPTION OF THE PREFERRED EMBODIMENTS

Figure 1:
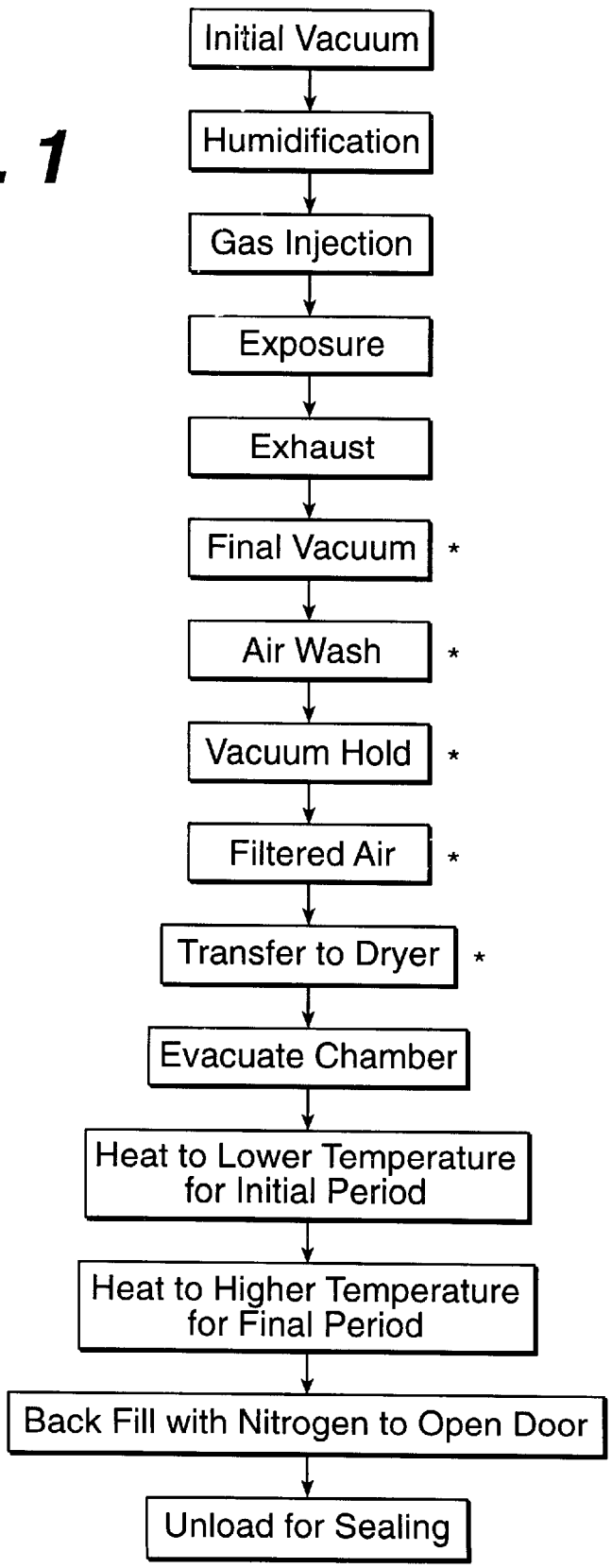
FIG. 1 is a flow diagram of a sterilization process of the present invention using ethylene oxide as a sterilant gas.

The sterilant gases that can be used in the practice of the present invention include conventional sterilant gases such as ethylene oxide, hydrogen peroxide, gluteraldehyde, paracetic acid, chlorine dioxide and the like. The diluent gases, which can be used in the practice of the process of the present invention in admixture with the sterilant gases include conventionally known inert diluent gases such as nitrogen, chlorofluorocarbons such as Freon® and Genetron™, carbon dioxide, argon and the like. The sterilant gases will contain a sufficiently effective amount of diluent gas to render the gas mixture non-flammable and non-explosive. The amount of diluent gas used will depend upon the nature of the sterilant gas, the configuration of the sterilizer, the sterilization cycle, etc. For example, when using ethylene oxide sterilant gas, the amount of diluent gas will typically range from about 5 wt. % to about 95 wt. %, more typically about 50 wt. % to about 95 wt. %, and preferably about 90 wt. % to about 92 wt. %; while the amount of ethylene oxide gas will typically range from about 5 wt. % to about 95 wt. %, more typically about 5 wt. % to about 50 wt. %, and preferably about 8 wt. % to about 10 wt. %.

The synthetic absorbable polymer materials that can be sterilized using the sterilization process of the present invention include conventional bioabsorbable polymers such as aliphatic polyesters, polylactides, polylactic acid, polydioxanone, polycaprolactone, polyglycolide, polygalactic acid, polyparadioxanone, and the like and copolymers and combinations thereof. The pouches, which are used to package the sutures of the present invention, include conventional pouches such as resin foil laminates, and Tyvek® spun bonded polyethylene, paper and the like and combinations thereof. The pouches may be sealed prior to sterilization in the case of spun Tyvek® bonded polyethylene pouches, or may be aseptically sealed after sterilization in the case of certain foil and Tyvek® pouches.

The sterilizer units useful in the practice of the present invention include conventional commercially available units such as those manufactured by Amsco and E.T.C. The sterilizer units typically consist of a large rectangular, jacketed vessel equipped with an entrance door at one end (generally the non-sterile or "dirty side") and an exit door on the other (generally the sterile or "clean side"). Typical connections to the inner space of the vessel include but are not limited to one or more ports for injecting steam or water vapor, sterilizing gasses, diluent gasses and exhausting the vessel through atmospheric or vacuum means. Typical control systems include but are not limited to temperature control, pressure control and vacuum control. Loading and unloading of the vessel can be by manual or automatic means depending on the nature of the operation.

A flow diagram of an ethylene oxide sterilization process of the present invention is seen in FIG. 1. The initial step in the process is to insert a bioabsorbable medical device, such as a suture, packaged in a pouch into the chamber of a sterilizer unit. The access doors to the chamber are then closed, providing the chamber with a gas-tight seal. Then the chamber is evacuated using a vacuum source to provide an effectively low pressure sufficient to effectively remove air from the chamber and the package. The vacuum is typically about 1 kPaA to about 10 kPaA, more typically about 2 kPaA to about 4 kPaA and preferably about 3 kPaA to about 4 kPaA. When the desired vacuum level has been reached and maintained for a sufficiently effective amount of time, humidity is injected into the chamber by a steam source. A sufficient amount of steam is injected to provide for a humidity level of about 50% to about 100%, more typically about 60% to about 95%, and preferably about 75% to about 85%. Next, the temperature of the interior of the chamber is raised to a sufficient temperature to effectively increase the reactivity of the sterilant gas. The desired temperature level may be obtained, for example, by adjusting the pressure within the chamber. Pressure may be adjusted by continuously operating a vacuum pump while simultaneously injecting steam at a rate sufficient to establish a steady state pressure at a level sufficient to obtain the desired chamber temperature. Typically, the temperature will be raised to a level of about 20° C. to about 50° C., more typically about 25° C. to about 40° C., and preferably about 30° C. to about 35° C. Then, a sufficient amount of ethylene oxide sterilant gas mixture (or another conventional gas sterilant mixture) is injected into the chamber to effectively sterilize the bioabsorbable devices and the interiors of the packages. Typically, the sterilant gas mixture will be added to maintain a chamber concentration of sterilant gas of about 500 mg/l to about 1,400 mg/l, more typically about 750 mg/l to about 1,200 mg/l, and preferably about 850 mg/l to about 1,000 mg/l. The sterilant gas mixture will be maintained in the chamber 15 for a sufficient amount of time to effectively sterilize the sutures. Typically, the sterilant will reside in chamber 15 for about 1 hour to about 24 hours, more typically about 3 hours to about 16 hours, and preferably about 4 hours to about 10 hours. It should be noted that the sterilant gases other than ethylene oxide may vary the cycle parameters and may require different residence times. Next, the chamber is evacuated to remove sterilant gas by connecting the chamber to a vacuum source. Optionally, the additional conventional steps of air washing and final vacuum are included in the cycle prior to degassing. Then the sutures are subjected to a first degassing step by lowering the chamber pressure and maintaining the chamber interior at a first temperature of about 45° C. to about 65° C., more typically about 50° C. to about 60° C., and preferably about 53° C. to about 57° C. for a sufficient amount of time to effectively remove substantially all of the residual moisture. The amount of time required for the first degassing cycle will be typically about 2 hours to about 12 hours, more typically about 3 hours to about 8 hours, and preferably about 3.5 hours to about 4.5 hours. The chamber pressure will typically be about 1,000 PaA to about 200 PaA, more typically about 800 PaA to about 400 PaA, and preferably about 650 PaA to about 500 PaA. At the end of the first degassing cycle, a second degassing cycle is initiated by raising the temperature of the interior of the chamber to a second higher sufficiently effective temperature and maintaining the temperature for a sufficient amount of time to effectively remove (down to conventionally accepted levels) residual sterilant gas, diluent, sterilization by-products and moisture from the devices and packages. The temperature of the second degassing cycle will typically be maintained at about 60 C to about 75 C, more typically about 62 C to about 72 C and preferably about 65 C to about 69 C. The length of time of the second degassing cycle will preferably be about 2 hours to about 12 hours, more typically about 3 hours to about 8 hours and preferably about 3.5 hours to about 4.5 hours. The chamber pressure will typically be about 60 PaA to about 1 PaA, more typically about 40 PaA to about 1 PaA, and preferably about 2 PaA to about 1 PaA. At the end of the second degassing cycle the sterilization cycle is complete, the chamber is raised to atmospheric pressure and allowed to cool off to ambient temperature. When is convenient to remove the medical device and pouch from the chamber, the chamber pressure is raised slightly above atmospheric pressure to aid in the opening of the chamber door. This may be achieved by backfilling the chamber with dry nitrogen gas. Any remaining cooling to ambient temperature may then take place. Pouches containing the medical devices are then processed in one of two ways, depending upon the construction of the package. If pouch is a foil pouch, the pouch must then be aseptically sealed prior to placing in finished goods storage. Although, certain foil pouches do not require aseptic sealing. If pouch is a conventional sealed gas permeable pouch, it may then be directly placed in finished goods storage. It should be noted that although it is possible to conduct one or more of the degassing steps in the sterilizer chamber, it is preferred to remove the sterilized, medical devices with pouches from the sterilizer prior to degassing and to conduct degassing steps in a separate conventional degassing chamber. If a separate degassing chamber is to be used some additional processing steps, as mentioned previously, may be required after the sterilant gas is evacuated from the chamber. These steps include drawing a final vacuum in the chamber followed by flushing the chamber with a microbiologically filtered diluent gas such as air. A second vacuum is then established in the chamber where the medical device may remain in storage for up to 72 hours. The chamber is then backfilled with filtered air to raise the chamber pressure to slightly above ambient pressure to aid opening the chamber door. The contents of the chamber are then transferred to a second chamber and vacuum degassed in this second chamber. The packages containing sutures are then processed in one of two ways, depending upon the construction of the package. If the package is a foil package, the package may then be aseptically sealed (if necessary) or otherwise sealed prior to placing it in finished goods storage. If package is a Tyvek® conventional sealed gas permeable pouch, it may then be directly placed in finished goods storage. It should be noted that although it is possible to conduct the degassing steps of the cycle in the sterilizer, it is preferred to remove the sterilized, packaged medical devices from the sterilizer prior to degassing and to perform the degassing steps in a conventional degassing chamber.

A flow diagram of an ethylene gas sterilization process of the prior art that is used to sterilize bioabsorbable sutures is seen in FIG. 2 and described in Example 1. The prior art process is similar to that of the present invention but only utilizes one degassing cycle. This degassing cycle is conducted at a temperature and pressure similar to that of the first degassing cycle of the present invention. However, the duration of this cycle is typically longer.

In that prior art process, the steps are similar to the steps of the present invention up to the point wherein the material is degassed. At that point, the pressure is reduced to a level sufficient to begin removing moisture and then increasing the temperature towards the final set point, generally around 50° C. to 55° C. The temperature is maintained at that preset value while the vacuum is continuously decreased to the greatest degree obtainable. While maintaining the temperature constant, the material is vacuum dried for a time sufficient to remove the moisture, residual sterilant gas and diluent gas to conventionally acceptable levels. This may require up to 24–32 hours depending on the nature of the materials being processed.

The following examples are illustrative of the principles and practice of the present invention compared to the prior art although not limited thereto.

EXAMPLE 1

Using a conventional prior art process, 100 dozen packages containing absorbable suture (polylactic acid/polygalactic acid copolymer) were placed into a chamber of sterilizer unit manufactured by Amsco. Then, the chamber doors were closed to provide a gas-tight seal and the chamber was evacuated to a pressure of less than 4 kPaA and held at that pressure for less than 30 minutes. Then, steam was injected into the chamber while the vacuum system was running to bring the overall temperature to 21° C. to 37° C. while maintaining the pressure at 1–4 kPaA. Sterilant gas (ethylene oxide) was then introduced commingled with diluent gas (Genetron™) until the pressure was raised to 227 to 250 kPaA. The temperature was then adjusted to 32–37° C. The chamber was maintained under these conditions for a minimum of 9 hours at which time the chamber was exhausted and flushed with microbiologically filtered diluent gas. The contents of the chamber were transferred to a second chamber and vacuum dried in this second chamber. In this chamber the pressure was reduced to less than 666 PaA and the temperature raised to 53° C. to 57° C. While maintaining the same temperature range the pressure in the vessel was continuously reduced to less than 20 PaA over a 24 to 32 hour period required to effectively reduce the sterilant gas, diluent gas and residual moisture to acceptable levels.

EXAMPLE 2

Utilizing the process of the present invention, 100 dz. absorbable sutures identical to those used in Example 1 were sterilized in a manner similar to that illustrated by Example 1, and then transferred to a second chamber for vacuum drying or degassing. Herein the pressure was reduced again to less than 666 kPaA and the temperature raised to 530° C. to 570° C. At the end of only four hours, although a large amount of residual moisture and other components were still present in the material, the temperature was raised to 65° C. to 690° C. While continuously reducing the chamber pressure to less than 20 PaA while maintaining the chamber temperature at 65° C. to 69° C., the material was dried for an additional four hours. At the end of that time period it was found that the sterilant gas, diluent gas and residual moisture were reduced to acceptable levels with no degradation of the sutures.

The advantages of the present invention over the sterilization cycles of the prior art are numerous and include the reduction of degassing cycle times resulting in improved productivity and resource utilization, and surprisingly, without degrading the sterile, packaged bioabsorbable medical devices. In addition, the use of the sterilization cycles of the present invention using the novel degassing cycles of the present invention may produce sterile, packaged bioabsorbable medical devices with lower amounts of residual moisture than prior art processes.

Although this invention has been shown and described with respect to detailed embodiments thereof, it will be understood by those skilled in the art that various changes in form and detail and sequence of steps thereof may be made without departing from the spirit and scope of the claimed invention.

What is claimed is:

1. A process for sterilizing a bioabsorbable medical device using a sterilant gas mixture, comprising the steps of:

providing an bioabsorbable medical device in a pouch;

placing the bioabsorbable medical device and pouch in a chamber of a gas sterilizer;

pulling a first vacuum on the chamber;

injecting moisture into the chamber;

charging a sterilant gas comprising a gas mixture of a sterilizing gas and an inert diluent gas into the chamber and maintaining the gas mixture in the chamber for a sufficient time to effectively sterilize the bioabsorbable medical device;

pulling a second vacuum on the chamber;

moving the medical device to a degassing chamber;

then degassing the bioabsorbable medical device and pouch for a first degassing cycle by subjecting the bioabsorbable medical device and pouch to a vacuum at a first sufficiently effective temperature for a sufficient time to effectively remove substantially all of the moisture from the bioabsorbable medical device; and, then degassing the bioabsorbable medical device for a second degassing cycle by maintaining the vacuum and subjecting the bioabsorbable medical device and pouch to a second sufficiently effective temperature, which is greater than said first temperature, said second temperature being maintained for a sufficient time to effectively remove substantially all of residual sterilant gas, diluent gas, sterilization byproducts, and moisture from the bioabsorbable medical device and pouch.

2. The process of claim 1, wherein the sterilant gas is selected from the group consisting of ethylene oxide, hydrogen peroxide, formaldehyde, chlorine dioxide, gluteraldehyde and paracetic acid.

3. The process of claim 1 wherein the diluent is selected from the group consisting of nitrogen, carbon dioxide, argon and cholorfluorocarbons.

4. The process of claim 1 wherein the pouch is a foil pouch having an unsealed end.

5. The process of claim 1 wherein the pouch is a sealed pouch comprising spun bonded polyethylene.

6. The process of claim 1 wherein the moisture injected into the chamber comprises steam.

7. The process of claim 1 wherein the bioabsorbable medical device comprises a bioabsorbable surgical suture.

8. The process of claim 1 wherein the bioabsorbable medical device comprises a copolymer of polylactic acid and polygalactic acid.

9. The process of claim 1 wherein the bioabsorbable medical device comprises a polyparadioxanone polymer.

10. The process of claim 1 wherein the chamber is subjected to a sterilant gas removal and air wash step prior to the degassing step.

11. The process of claim 1, wherein the bioabsorbable medical device is selected from the group consisting of polylactide, polylactic acid, polydioxanone, polycaprolactone, polyglycolide and copolymers and mixtures thereof.

12. The process of claim 1, wherein the sterilizing gas is ethylene oxide gas.

13. The process of claim 1, wherein the first degassing step and the second degassing step are conducted in the gas sterilizer chamber.

14. The process of claim 1, wherein the first degassing step and the second degassing step are conducted in a degassing chamber, which is different than the gas sterilizer chamber.

15. The process of claim 1, wherein said second temperature is in a range of from about 60 degrees Celsius to about 75 degrees Celsius.

16. The process of claim 1, wherein said first temperature is in a range of from about 45 degrees Celsius to about 65 degrees Celsius.

17. The process of claim 1, wherein said second temperature is in a range of from about 62 degrees Celsius to about 72 degrees Celsius.

18. The process of claim 1, wherein said first temperature is in a range of from about 50 degrees Celsius to about 60 degrees Celsius.

19. The process of claim 1, wherein said second temperature is in a range of from about 65 degrees Celsius to about 69 degrees Celsius.

20. The process of claim 1, wherein said first temperature is in a range of from about 53 degrees Celsius to about 57 degrees Celsius.

21. The process of claim 1, wherein the second degassing step is conducted for a length of time in a range of from about 2 hours to about 12 hours.

22. The process of claim 21, wherein the first degassing step is conducted for a length of time in a range of from about 2 hours to about 12 hours.

23. The process of claim 1, wherein the second degassing step is conducted for a length of time in a range of from about 3 hours to about 8 hours.

24. The process of claim 23, wherein the first degassing step is conducted for a length of time in a range of from about 3 hours to about 8 hours.

25. The process of claim 1, wherein the second degassing step is conducted for a length of time in a range of from about 3.5 hours to about 4.5 hours.

26. The process of claim 25, wherein the first degassing step is conducted for a length of time in a range of from about 3.5 hours to about 4.5 hours.

27. The process of claim 1, wherein the second degassing step is conducted at a pressure in a range of from about 60 PaA to about 1 PaA.

28. The process of claim 1, wherein the second degassing step is conducted at a pressure in a range of from about 40 PaA to about 1 PaA.

29. The process of claim 1, wherein the second degassing step is conducted at a pressure in a range of from about 2 PaA to about 1 PaA.

* * * * *